United States Patent [19]
Ohta et al.

[11] Patent Number: 6,110,440
[45] Date of Patent: *Aug. 29, 2000

[54] FLUIDIZED-BED REACTOR AND REACTION PROCESS USING THE SAME

[75] Inventors: Masanobu Ohta, Gunma; Morihide Yokura, Tokyo, both of Japan

[73] Assignee: Asahi Kasei Kogyo Kabushiki Kaisha, Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/875,283
[22] PCT Filed: Jan. 30, 1996
[86] PCT No.: PCT/JP96/00171
  § 371 Date: Jul. 23, 1997
  § 102(e) Date: Jul. 23, 1997
[87] PCT Pub. No.: WO96/23582
  PCT Pub. Date: Aug. 8, 1996

[30] Foreign Application Priority Data

Feb. 1, 1995 [JP] Japan .................................... 7-015272

[51] Int. Cl.[7] .............................. B01J 8/22; C01B 21/00; C07C 253/24
[52] U.S. Cl. .......................... 423/351; 422/139; 422/143; 422/231; 558/319
[58] Field of Search ..................................... 422/143, 139, 422/231; 137/561 R; 423/237, 351, 364; 588/205; 558/319

[56] References Cited

U.S. PATENT DOCUMENTS

| 4,580,597 | 4/1986 | Cordingley et al. ............... 137/561 |
| 5,256,810 | 10/1993 | Rowe et al. . |

FOREIGN PATENT DOCUMENTS

| 230309 | 7/1987 | European Pat. Off. . |
| 446379 | 9/1991 | European Pat. Off. . |
| 1194405 | 9/1959 | France . |
| 2258 | 1/1990 | Japan . |
| 6211768 | 8/1994 | Japan . |
| 1265770 | 7/1970 | United Kingdom . |

Primary Examiner—Hien Tran
Attorney, Agent, or Firm—Birch, Stewart, Kolasch & Birch, LLP

[57] ABSTRACT

A fluidized-bed reactor for ammo-oxidation or oxidation and an ammo-oxidation or oxidation process using the reactor. The reactor comprises a vessel, a sparger for supplying and dispersing a gas containing an organic material, and a distributor for supplying and dispersing an oxygen-containing gas, the sparger comprising a header and a plurality of dispersion pipes connected laterally to the header, the dispersion pipes each having a plurality of orifices, wherein the hole size of an orifice farthest from the header is larger than the hole size of an orifice nearest the header, and the hole size of one orifice is larger than or equal to the hole size of adjacent orifice that is nearer the header than the one orifice.

8 Claims, 2 Drawing Sheets

FLUIDIZED-BED REACTOR AND REACTION PROCESS USING THE SAME

TECHNICAL FIELD

The present invention relates to a fluidized-bed reactor for ammo-oxidation or oxidation, and an ammo-oxidation or oxidation process using the same.

BACKGROUND ART

Ammo-oxidation or oxidation has been carried out industrially for a long time, and a large number of fluidized-bed reactors used therefor have been proposed. The structure of a sparger for supplying and dispersing a raw material therefor, however, has been only disclosed in British Patent No. 1,265,770, JP-A-2-258, JP-A-6-211768, etc. (The term "JP-A" used herein means an unexamined published Japanese patent application.)

The former two, British Patent No. 1,265,770 and JP-A-2-258, are designed so that oxygen gas outlet orifices and propylene/ammonia outlet orifices are made to be opposite to each other, i.e., one oxygen gas outlet orifice directly faces one propylene/ammonia outlet orifice with both orifices aligning on the same axis, but there is no recognition concerning the hole size of the orifices. The latter, JP-A-6-211768, relates to a method of keeping the temperature of ammonia in conduit pipes to be not higher than the dissociation point thereof in order to prevent the nitrization of the supply conduit pipes. Specifically, the latter proposes to provide a protective layer of a heat insulating material in each of the conduit pipes, but there is no recognition concerning the hole size of orifices as similar to the former two.

DISCLOSURE OF THE INVENTION

An object of the present invention is to provide a fluidized-bed reactor in which the yield of reaction is improved by controlling the molar ratio distribution of reaction gases locally arranged in the reactor in the ammo-oxidation or oxidation reaction, particularly, in the case where the reaction gases are separately supplied through two systems.

Another object of the present invention is to provide an ammo-oxidation or oxidation process using the above reactor.

Other objects and effects of the present invention will be apparent from the following description.

The present invention relates to a fluidized-bed reactor for ammo-oxidation or oxidation comprising a vessel, a sparger for supplying and dispersing a gas containing an organic material, and a distributor for supplying and dispersing an oxygen-containing gas, the sparger comprising a header and a plurality of dispersion pipes connected laterally to the header, the dispersion pipes each having a plurality of orifices, wherein the hole size of an orifice farthest from the header is larger than the hole size of an orifice nearest the header, and the hole size of one orifice is larger than or equal to the hole size of adjacent orifice that is nearer the header than the one orifice.

The present invention also relates to an ammo-oxidation or oxidation process comprising the step of ammo-oxidizing or oxidizing an organic material in the above fluidized-bed reactor.

BEST MODE FOR PRACTICING THE INVENTION

The ammo-oxidation or oxidation to be applied to the present invention is not particularly limited. Examples of the ammo-oxidation or oxidation include ammo-oxidation by which propylene, butene or propane is made to react with ammonia and oxygen to thereby produce corresponding nitrile; oxidation by which propylene, butene or propane is made to react with oxygen to thereby produce oxide; oxidation such as chloro-oxidation reaction; and the like reactions. The fluidized-bed reactor according to the present invention is aimed at an industrially practical apparatus.

The fluidized-bed reactor of the present invention will be described below by referring to the attached drawings, but the present invention is not construed as being limited thereto.

Figure 1:
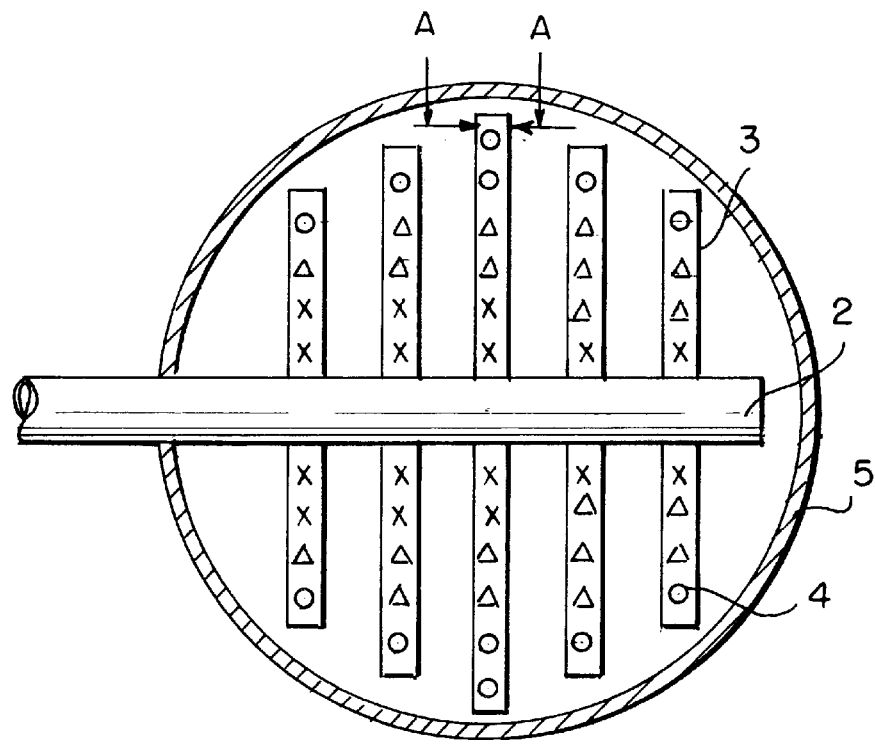
FIG. 1 is a schematic view showing an example of a sparger of a fluidized-bed reactor according to the present invention.
Figure 2:
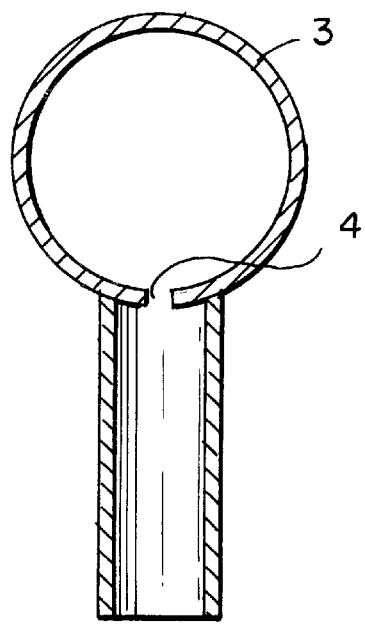
FIG. 2 is a schematic sectional view of an orifice taken along the line A—A of FIG. 1.

FIG. 1 is a schematic sectional view showing one embodiment of a sparger of a fluidized-bed reactor according to the present invention. The sparger for supplying and dispersing oxygen and/or a raw material has a large number of dispersion pipes 3 connected successively laterally to a header 2. Each of the dispersion pipes has a large number of orifices 4 which serve as gas outlets. The respective hole sizes of the orifices are designed so that an orifice located in a position farther from the header has a larger hole size. Numeral 5 denotes a vessel wall of the reactor. FIG. 2 is a schematic sectional view of the orifice.

Although FIG. 1 shows an embodiment where the header crosses the sparger, an auxiliary header extending laterally from the middle of the header may be provided so that the headers are shaped like a cross if the sparger is large. The number of dispersion pipes connected laterally to the header varies in accordance with the size of the sparger, that is, in accordance with the size of the fluidized-bed reactor. The number of dispersion pipes may be generally from about 10 to about 300, preferably from about 20 to about 200.

The number of orifices in each dispersion pipe may be determined in accordance with the length of the dispersion pipe or in accordance with the setting of the region which is to be covered by the orifices. Generally, it is preferable that the number of orifices is from about 1 to about 4 in the case of a short dispersion pipe, while it is from about 4 to about 50 in the case of a long dispersion pipe. In the present invention, the hole sizes of the orifices are designed so that an orifice nearer the outer circumferential portion of the sparger has a larger hole size. Preferably, the ratio of the maximum hole size of orifice to the minimum hole size of orifice is in the range of from about 1.02 to about 1.3. The hole size may be changed continuously or may be changed stepwise so that several orifices have the same hole size. The number of orifices that have a different hole size from the other orifices is preferably at least 10%, more preferably at least 50%, based on the total number of orifices. The hole size of an orifice is generally selected from the range of from 1.5 to 20 mm.

The present inventors have made extensive investigation and found the following fact. That is, in ammo-oxidation or oxidation reaction in a fixed-bed reactor, the molar ratio of reaction gases has large influence on the yield of reaction, so that there is a proper molar ratio of the reaction gases. If such a reaction is conducted in a fluidized-bed reactor in which reaction gases are separately supplied through two systems, for example, in the case of ammo-oxidation, the molar ratio of reaction gases is as follows: When oxygen or air is supplied from one system and propylene and an ammonia gas are supplied from the other system, the local molar ratio distribution of the reaction gases in the fluidized-bed reactor becomes important. If the local molar ratio distribution is uniform throughout the reactor, it is possible to set a proper molar ratio on the whole of the reactor. However, if the local molar ratio distribution is not uniform, the yield on the whole of the reactor becomes low because the interior of the reactor is separated into a region in which a large amount of unreacted olefin is left due to shortage of oxygen, and a region in which a large amount of by-product is produced due to excess of oxygen.

The local molar ratio can be made uniform by making the amount of gas blown out of dispersion pipe orifices uniform. According to the analysis by the present inventors, it has been found that the factor having large influence on the amount of gas blown out is gas temperature rising in the sparger, and that, in some case, the temperature difference between a portion near the reactor inlet of the sparger and a portion far therefrom becomes 50 to 200° C. or higher. The degree of gas temperature rising varies depending on the length of the header, the respective lengths of the dispersion pipes, the difference in temperature between the fluidized bed and the supply gas, or the like. On the other hand, it has been found that the loss of pressure in the header and in the dispersion pipes is generally low and has little influence on the difference in amount between gasses blown out. It has been further found that the change of the flow coefficient caused by the difference between the respective hole sizes of orifices is so small as to be neglected and that the same flow coefficient may be used.

Hence, the respective amounts of gases blown out of orifices may be made uniform if the respective hole sizes of the orifices are changed in accordance with the respective temperatures of the gases in the dispersion pipes. The relationship between the hole size and the gas temperature can be given by the following equation (1):

$$D \; T^{1/4} \tag{1}$$

in which D represents the hole size of an orifice, and T represents the temperature of gas in each orifice and is expressed in absolute temperature (K).

The gas temperature T is in the range of from the temperature of the gas supplied in the reactor inlet to the temperature of the gas in an end of the sparger. In some cases, the gas temperature T distributes in a range of from 300 to 650 K. The gas temperature T can be determined by general calculation of heat transmission or by actual measurement. The rising of the gas temperature T is generally constituted by the temperature rising in the header and the temperature rising in each dispersion pipe. Consequently, the respective amounts of reaction gases blown out of the orifices can be made uniform when the respective hole sizes of orifices in the dispersion pipes are designed so that an orifice farther from the header has a larger hole size as described above.

The distributor for supplying and dispersing an oxygen-containing gas is not particularly limited and may be, e.g., a perforated plate or a sparger. For example, the distributor for supplying and dispersing an oxygen-containing gas may be a sparger having a constitution similar to the sparger for supplying and dispersing the organic material-containing gas.

Figure 3:
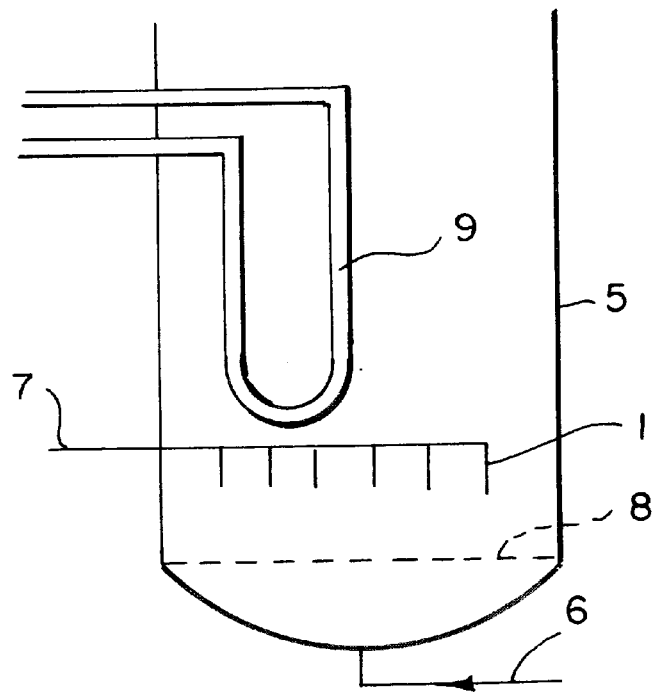
FIG. 3 is a schematic vertical sectional view of an example of a fluidized-bed reactor which is a subject of the present invention.

In the case where an oxygen-containing gas is dispersed by a perforated plate 8 as shown in FIG. 3, the temperature of the gas is nearly uniform. In this case, the amount of oxygen blown out can be made nearly uniform if the respective hole sizes of all the orifices are made equal. On the other hand, in an organic material mixture gas sparger 1, it is important that the uniform amount of gas blown out is obtained by changing the orifice hole size in accordance with the gas temperature distribution in the inside of the sparger. Numeral 6 denotes an oxygen inlet pipe, 7 denotes an organic material mixture gas inlet pipe, and 9 denotes a cooling coil.

Figure 4:
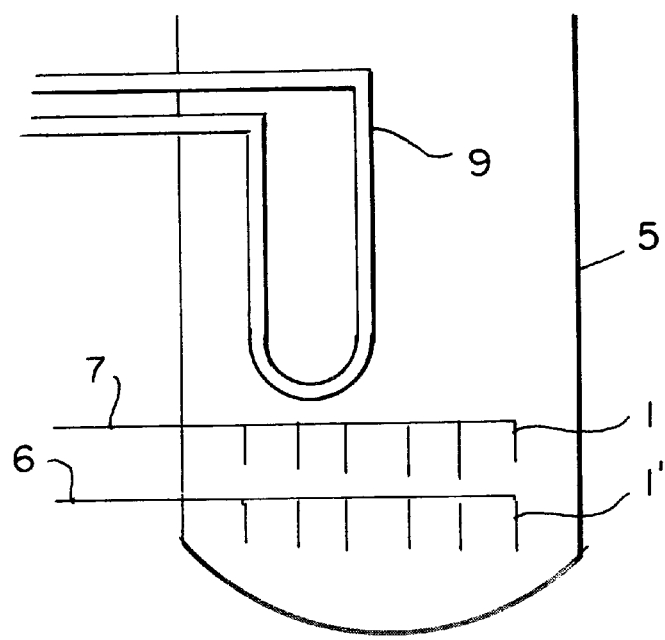
FIG. 4 is a schematic vertical sectional view of another example of a fluidized-bed reactor which is a subject of the present invention.

In the case where an organic material-containing gas is dispersed by a sparger 1 and similarly an oxygen-containing gas is dispersed by a sparger 1' as shown in FIG. 4, it is important that the orifice hole size is changed in accordance with the gas temperature in the inside of the spargers 1 and 1' so that both the amount of the oxygen-containing gas blown out and the amount of the organic material mixture gas blown out are made uniform, respectively. Particularly, in the case where the oxygen-containing gas is a main gas for fluidizing the bed, uniform blowing-out is essential to form a good fluid state.

Any known catalyst for ammo-oxidation or oxidation may be used as a catalyst in the present invention. Further, any known condition as described in a lot of known literatures and patents may be employed as a reaction condition in the present invention. For example, the condition of ammo-oxidation for production of α,β-unsaturated nitrile may be as follows: A raw-material oxygen-containing gas (air) to be supplied to the reactor is used in an amount of from 5 to 15 moles, preferably in a range of from 7 to 14 moles, per mole of olefin or tertiary alcohol, and ammonia is used in an amount of from 1 to 2 moles, preferably from 1 to 1.5 moles, per mole of olefin or tertiary alcohol. The reaction temperature is in the range of from 350 to 600° C., preferably in the range of from 400 to 500° C., the pressure is not higher than 3 $Kg/cm^2$ G, preferably in the range of from 0.2 to 1.5 $Kg/cm^2$ G, and the contact time is in the range of 1 to 15 seconds, preferably in the range of from 2 to 6 seconds.

EXAMPLE

The present invention will be further described below by referring to Examples of the present invention and Comparative Example, but the present invention is not construed as being limited thereto.

In the Examples and Comparative Example, unreacted olefin contained in a reaction gas was analyzed by gas chromatography. The reaction gas was sampled by a manner in that gas sampling nozzles were provided at a position of r/R=0.0 (in which r represents the distance from the center of the reactor, and R represents the radius of the reactor) in the center portion at a height of 9 m, and at a position of r/R=0.9 in the outer circumferential portion of the same height, respectively, and that gases blown out of the nozzles were washed with water and then picked out. The constitution of the reactor and the reaction conditions other than those specifically described were in the range generally employed and would not influence the results of the reaction.

Example 1 and Comparative Example 1

The diameter of the reactor used was 7.8 m. The catalyst used was a molybdenum-bismuth-iron carrier catalyst having a particle size of from 10 to 100 μm and an average particle size of 50 μm. The reactor was filled with the catalyst so that the height of the stationary layer became 3 m. As an air dispersion plate, there was used a dispersion plate having orifices identical in hole size with each other. A mixture gas of propylene and ammonia was introduced by using a sparger having orifices which were designed so that an orifice farther from the header had a larger hole size as shown in FIG. 1. The respective hole sizes of the orifices were classified into three kinds, i.e., the maximum hole size (represented by the symbol o in FIG. 1), the intermediate hole size (represented by the symbol Δ in FIG. 1), and the minimum hole size (represented by the symbol x in FIG. 1). The ratio of the maximum hole size to the minimum hole size was 1.15. The total number of the holes of orifices was 640. The number of maximum-hole-size orifices, the number of intermediate-hole-size orifices and the number of minimum-hole-size orifices were selected to be 96, 232 and 232, respectively.

While 41,000 $NM^3/H$ of air, 4,000 $NM^3/H$ of propylene and 4,800 $NM^3/H$ of ammonia were supplied from the lower portion of the fluidized bed and made to react with each other in the condition of reaction temperature of 450° C. and pressure of 1 $Kg/cm^2$ G. Thus, results shown in Table 1 (Example 1) were obtained.

Separately, the same reaction was conducted by using a sparger having orifices which are identical in hole size with each other. Thus, results shown in Table 1 (Comparative Example 1) were obtained.

In Example 1, the amount of unreacted propylene in the center portion and the amount of $CO_2$ in the outer circumferential portion were greatly reduced in comparison to Comparative Example 1.

Example 2

The diameter of the reactor used was 5.3 m. The catalyst used was a molybdenum-bismuth-iron carrier catalyst having a particle size of from 10 to 100 μm and an average particle size of 50 μm. The reactor was filled with the catalyst so that the height of the stationary layer became 3 m. As an air dispersion plate, there was used a dispersion plate having orifices identical in hole size with each other. A mixture gas of isobutylene and ammonia was introduced by using a sparger having orifices which were designed so that an orifice farther from the header had a larger hole size. The respective hole sizes of the orifices were classified into three kinds. The ratio of the maximum hole size to the minimum hole size was 1.10. The total number of the holes of orifices was 331. The number of maximum-hole-size orifices, the number of intermediate-hole-size orifices and the number of minimum-hole-size orifices were selected to be 101, 95 and 135, respectively.

While 23,000 $NM^3/H$ of air, 2,300 $NM^3/H$ of isobutylene and 3,000 $NM^3/H$ of ammonia were supplied from the lower portion of the fluidized bed and made to react with each other in the condition of reaction temperature of 430° C. and pressure of 1 $Kg/cm^2$ G. Thus, results shown in Table 1 were obtained.

Example 3

The diameter of the reactor used was 5.3 m. The catalyst used was a molybdenum-bismuth-iron carrier catalyst having a particle size range of from 10 to 100 μm and an average particle size of 50 μm. The reactor was filled with the catalyst so that the height of the stationary layer became 3 m. As an air dispersion plate, there was used a dispersion plate having orifices identical in hole size with each other. A mixture gas of propylene and ammonia was introduced by using a sparger having orifices which were designed so that an orifice farther from the header had a larger hole size. The respective hole sizes of the orifices were classified into three kinds. The ratio of the maximum hole size to the minimum hole size was 1.10. The total number of the holes of orifices was 315. The number of maximum-hole-size orifices, the number of intermediate-hole-size orifices and the number of minimum-hole-size orifices were selected to be 61, 134 and 120, respectively.

While 20,500 $NM^3/H$ of air, 2,000 $NM^3/H$ of propylene and 2,400 $NM^3/H$ of ammonia were supplied from the lower portion of the fluidized bed and made to react with each other in the condition of reaction temperature of 450° C. and pressure of 1 $Kg/cm^2$ G. Thus, results shown in Table 1 were obtained.

TABLE 1

|  | Center portion | | Circumferential portion | |
| --- | --- | --- | --- | --- |
|  | Unreacted propylene or isobutylene (vol %) | $CO_2$ (vol %) | Unreacted propylene or isobutylene (vol %) | $CO_2$ (vol %) |
| Example 1 | 0.06 | 1.62 | 0.07 | 2.88 |
| Comparative Example 1 | 0.15 | 1.64 | 0.09 | 2.52 |
| Example 2 | 0.07 | 2.23 | 0.08 | 2.44 |
| Example 3 | 0.09 | 1.74 | 0.10 | 1.85 |

In the present invention, the respective hole sizes of orifices in a sparger of a fluidized-bed reactor for ammo-oxidation or oxidation are designed so that an orifice farther from the header has a larger hole size, by which the molar ratio distribution of reaction gases is made uniform to improve the yield of reaction.

What is claimed is:
1. A fluidized-bed reactor for ammo-oxidation or oxidation comprising a vessel, a sparger for supplying and dispersing a gas containing an organic material, and a distributor for supplying and dispersing an oxygen-containing gas, said sparger comprising at least one header and a plurality of dispersion pipes connected laterally to said header, said header entering the vessel through a side of the vessel, said dispersion pipes each having a plurality of orifices, so that hole sizes of the orifices are specified by an average diameter based on an area of a percentage of the orifices, wherein the hole size of an orifice farthest from said header is larger than the hole size of an orifice nearest said header, and the hole size of one orifice is larger than or equal to the hole size of an adjacent orifice that is nearer said header than said one orifice, and wherein a ratio of a maximum hole size orifice to a minimum hole size orifice is in a range of from 1.02 to 1.3, wherein a number of orifices of a given size is different for the dispersion pipe located farther from where the header enters the vessel than for the dispersion pipe located nearer to where the header enters the vessel, so that a first dispersion pipe located farther from where the header enters the side of the vessel, when compared to a second dispersion pipe located closer to where the header enters the side of the vessel, wherein both said first and second dispersion pipes have a same length, the number of the maximum size orifices of said first dispersion pipe is equal or larger than the number of the maximum size orifices of said second dispersion pipe.

2. A fluidized-bed reactor as claimed in claim 1, wherein said distributor for supplying and dispersing an oxygen-containing gas is a sparger comprising a header and a plurality of dispersion pipes connected laterally to said header of said distributor, said dispersion pipes of said distributor each having a plurality of orifices, wherein, in said distributor, the hole size of an orifice farthest from said header is larger than the hole size of an orifice nearest said header, and the hole size of one orifice is larger than or equal to the hole size of an adjacent orifice that is nearer said header than said one orifice.

3. A fluidized-bed reactor as claimed in claim 1, wherein the number of orifices that have a different hole size from the other orifices is at least 10% based on the total number of orifices.

4. A fluidized-bed reactor as claimed in claim 3, wherein the number of orifices that have a different hole size from the other orifices is at least 50% based on the total number of orifices.

5. An ammo-oxidation or oxidation process comprising the step of ammo-oxidizing or oxidizing an organic material in a fluidized-bed reactor, said fluidized-bed reactor comprising a vessel, a first sparger for supplying and dispersing a gas containing an organic material, and a distributor for supplying and dispersing an oxygen-containing gas, said first sparger comprising at least one first header and a plurality of first dispersion pipes connected laterally to said first header, said first header entering the vessel through a side of the vessel, said first dispersion pipes each having a plurality of first orifices, so that hole sizes of the first orifices are specified by an average diameter based on an area of a percentage of the first orifices, wherein the hole size of a first orifice farthest from said first header is larger than the a hole size of a first orifice nearest said first header, and the hole size of one first orifice is larger than or equal to the hole size of an adjacent first orifice that is nearer said first header than said one first orifice, wherein said distributor for supplying and dispersing an oxygen-containing gas is a second sparger comprising a second header and a plurality of second dispersion pipes connected laterally to said second header, said second dispersion pipes each having a plurality of second orifices, and wherein the hole size of a second orifice farthest from said second header is larger than the hole size of a second orifice nearest said second header, and the hole size of one second orifice is larger than or equal to the hole size of an adjacent second orifice that is nearer said second header than said one second orifice, wherein, in each sparger, a ratio of a maximum hole size orifice to a minimum hole size orifice is in a range of from 1.02 to 1.3, wherein a number of orifices of a given size is different for the dispersion pipe located farther from where the header enters the vessel than for the dispersion pipe located nearer to where the header enters the vessel, so that a first dispersion pipe located farther from where the header enters the side of the vessel, when compared to a second dispersion pipe located closer to where the header enters the side of the vessel, wherein both said first and second dispersion pipes have a same length, the number of the maximum size orifices of said first dispersion pipe is equal or larger than the number of the maximum size orifices of said second dispersion pipe.

6. An ammo-oxidation or oxidation process as claimed in claim 5, wherein the number of orifices that have a different hole size from the other orifices is at least 10% based on the total number of orifices.

7. An ammo-oxidation or oxidation process as claimed in claim 6, wherein the number of orifices that have a different hole size from the other orifices is at least 50% based on the total number of orifices.

8. An ammo-oxidation or oxidation process as claimed in claim 5, wherein the number of orifices that have a different hole size from the other orifices is at least 50% based on the total number of orifices.

* * * * *